United States Patent [19]

Deutsch

[11] Patent Number: 4,820,271
[45] Date of Patent: Apr. 11, 1989

[54] GUIDING CATHETER SYSTEM

[76] Inventor: Larry-Stuart Deutsch, 1940 Malcolm Ave., Apt. 102, Los Angeles, Calif. 90025

[21] Appl. No.: 76,064

[22] Filed: Jul. 21, 1987

Related U.S. Application Data

[63] Continuation of Ser. No. 839,927, Mar. 17, 1986, abandoned.

[51] Int. Cl.⁴ .................................. A61M 25/00
[52] U.S. Cl. ..................... 604/99; 128/344; 128/348.1; 604/4
[58] Field of Search ................. 604/96–103, 604/4, 51–53, 280; 128/344, 348.1

[56] References Cited

U.S. PATENT DOCUMENTS

| | | | |
|---|---|---|---|
| 3,044,468 | 7/1962 | Birtwell | 604/97 |
| 3,050,066 | 8/1962 | Koehn | 604/97 |
| 3,253,594 | 5/1966 | Matthews et al. | 604/96 |
| 3,913,565 | 10/1975 | Kawahara | 604/96 X |
| 4,024,873 | 5/1977 | Antoshkiw et al. | 604/96 |
| 4,195,637 | 4/1980 | Gruntzig et al. | 604/97 X |
| 4,284,081 | 8/1981 | Kasper et al. | 604/97 |
| 4,295,464 | 10/1981 | Shihata | 128/344 X |
| 4,370,982 | 2/2983 | Reilly | 604/99 |
| 4,381,765 | 5/1983 | Burton | 604/98 X |
| 4,437,856 | 3/1984 | Valli | 604/96 X |
| 4,445,892 | 5/1984 | Hussein et al. | 604/101 |
| 4,464,175 | 8/1984 | Altman et al. | 604/99 |
| 4,573,966 | 3/1986 | Weikl et al. | 604/101 X |
| 4,581,017 | 4/1986 | Sahota | 604/101 |
| 4,689,041 | 8/1987 | Corday et al. | 604/99 |

Primary Examiner—Dalton L. Truluck
Attorney, Agent, or Firm—Matthew F. Jodziewicz

[57] ABSTRACT

This invention discloses a catheter comprising a first hollow tubular body of flexible non-kinking material having an entry and an exit port and a first lumen therethrough. A fixation balloon of soft elastomeric material is attached coaxially to the first hollow tubular body proximate the exit port. A second hollow tubular body of flexible non-kinking material having a second lumen therethrough is operatively attached at one end to the fixation balloon and at a opposite second end to means to selectively inflate or deflate the fixation balloon by applying pressure to a liquid contained in the second lumen. The second lumen provides a passageway for communicating pressure to inflate or deflate the fixation balloon to a liquid between the fixation balloon and the selective inflation and deflation means. Means are operatively coupled to the selective inflation and deflation means to limit the pressure supplied to inflate the fixation balloon through the second lumen to a selected pre-set pressure limit. The first hollow tubular body may be comprised of porous material adapted to permit fluid flow therethrough or have a plurality of holes therethrough proximate said fixation balloon. The preferred liquid used to communicate the pressure to the fixation balloon is a dilute mixture of a radiographic contrast agent and saline. The fixation balloon may have an inflated shape adapted to resist backward movement of the first hollow tubular body from an opening once the fixation balloon is inserted into the target vessel ostium and inflated.

12 Claims, 1 Drawing Sheet

GUIDING CATHETER SYSTEM

This application is a continuation of application Ser. No. 06/839,927 filed Mar. 17, 1986 by the same inventor, now abandoned.

BACKGROUND OF THE INVENTION

1. Field of the Invention

This invention relates generally to a catheter, used to achieve stable selective catheterization of a vessel, that will function as a guiding catheter to permit the coaxial passage of other catheters and devices including Percutaneous Transluminal Coronary Angioplasty (PTCA) and non-coronary Percutaneous Transluminal Angioplasty (PTA) catheters through it into the catheterized vessel.

2. Description of the Prior Art

The design of a practical catheter system equipped with a balloon at its distal end for use in dilation of narrowed vascular structures is generally credited to Dr. Andreas Gruntzig although several balloon and non-balloon dilation catheters had been designed and used prior to Dr. Gruntzig's device. When the balloon portion of the catheter is inflated in a lesion such as a narrowed region of a vascular structure, a controlled injury is produced which increases the overall cross-sectional area of that vascular structure. This process is called Percutaneous Transluminal Coronary Angioplasty (PTCA) in the case of coronary arteries and Percutaneous Transluminal Angioplasty (PTA) in the case of non-coronary vascular structures (including vascular structures other than blood vessels). Although usually introduced into the body via a skin puncture (hence "percutaneous"), these catheters may also be introduced into the body via a surgical procedure appropriate to the area to which access is desired.

Balloon dilation catheters are made of many different materials and are made in many different sizes and shapes including different balloon lengths and diameters.

Some PTA catheters are made of sufficiently strong material that they can be used to catheterize a vessel without the use of any external support. Such catheters are advanced in vessels using only a coaxial inner guide wire support which is advanced into the vessel ahead of the catheter and stabilized in a manner that will permit the catheter to be slid into a desired location over the stabilized guide wire. However, small caliber PTA catheters and most PTCA catheters are so flexible that they require the use of a coaxial guiding catheter for external support. The distal end of the guiding catheter is placed in the vessel (or a vessel leading to the vessel) into which it is desired to place the PTCA/PTA catheter and the PTCA/PTA catheter advanced through this guiding catheter to the desired location (usually with the aid of a coaxial guide wire passed through the PTCA/PTA catheter).

One of the principal causes of technical failure in the performance of PTCA/PTA procedures is the inability to obtain a sufficiently stable guiding catheter position that will permit placement of the PTCA/PTA dilation catheter at the lesion site for the proposed PTCA/PTA procedure. When the force required to advance the PTCA/PTA dilation catheter through the vessel becomes greater than the forces which tend to keep the distal end of the guiding catheter in the vessel ostium, further efforts to advance the PTCA/PTA dilation catheter result in transmission of force to the guiding catheter in a direction such that the distal end of the guiding catheter is pushed backwards out of the vessel ostium and no further advancement of the PTCA/PTA dilation catheter occurs. This problem becomes particularly significant as the length and/or severity of narrowing of the lesion increase since these factors increase the frictional forces which tend to resist passage of the PTCA/PTA dilation catheter through the area of the lesion. Tortuosity of the PTCA/PTA target vessel or the vessels that must be traversed by the PTCA/PTA dilation catheter in order to reach the lesion site also tends to increase frictional resistance to the advancement of the PTCA/PTA dilation catheter. These problems become especially significant when the width and/or orientation of the aorta in the region of the vessel ostium or the course of the proximal vessel segment that must be traversed in order to reach the lesion site are such that catheterization with standard prior art PTCA/PTA guiding catheters proves difficult or unstable. This instability manifests itself as either simple inability to maintain the desired position of the PTCA/PTA guiding catheter long enough to accomplish the intended procedure or, more often, dislodging of the guiding catheter from the vessel ostium in the course of attempting to advance the PTCA/PTA dilation catheter as described above. This dislodging is commonly referred to as the "backing out" phenomenon.

When guiding catheters are used for the passage of devices other than angioplasty catheters, similar stability problems are encountered including the "backing out" phenomenon.

Current prior art guiding catheters do not provide a solution for these noted problems.

Prior art guiding catheters known to the Applicant and described above, are simple catheters having no provision to stabilize the guiding catheter at the ostium of the target vessel. In fact, the current problems noted above only arose with the introduction and use of the existing prior art guiding catheters.

The present invention discloses a solution to the problems noted above to be common with the prior art devices.

SUMMARY AND OBJECTS OF THE INVENTION

It is an object of the present invention to provide a catheter useful as a guiding catheter.

It is another object of the present invention to provide a catheter useful as a guiding catheter that provides adequate fixation of the distal end of the catheter with regard to a vessel ostium to obtain a sufficiently stable guiding catheter position that will permit placement of a coaxial dilation catheter or other device into the vessel or a branch thereof.

It is yet another object of the present invention to provide a catheter useful as a guiding catheter that provides adequate fixation of the distal end of the catheter with regard to a vessel ostium to obtain a sufficiently stable guiding catheter position that will eliminate the dislodging of the distal end of the guiding catheter from the vessel ostium in passing the coaxial dilation catheter or other device through the lumen of the guiding catheter and into the target vessel or a branch thereof (the "backing out" phenomenon).

Still another object of the present invention is to provide a catheter useful as a guiding catheter that is both safe and effective in use.

In summary, a catheter constructed in accordance with the invention disclosed and claimed herein, would comprise a first hollow tubular body of flexible non-kinking material having an entry and an exit port and a first lumen therethrough. A fixation balloon of soft elastomeric material is attached coaxially to the first hollow tubular body proximate the exit port. A second hollow tubular body of flexible non-kinking material having a second lumen therethrough is operatively attached at one end to the fixation balloon and at an opposite second end to means to selectively inflate or deflate the fixation balloon by applying pressure to a liquid contained in the second lumen. The second lumen provides a passageway for communicating pressure to inflate or deflate the fixation balloon to the liquid between the fixation balloon and the selective inflation and deflation means. Means may be operatively coupled to the selective inflation and deflation means to limit the pressure supplied to inflate the fixation balloon through the second lumen to a selected pre-set pressure limit. The first hollow tubular body may be comprised of porous material adapted to permit fluid flow therethrough or have a plurality of holes therethrough proximate said fixation balloon. The liquid used to communicate the pressure to the fixation balloon is a dilute mixture of a radiographic contrast agent and saline, or any other safe non-toxic fluid material. The fixation balloon may havē an inflated shape adapted to resist backward movement of the first hollow tubular body from an opening once the fixation balloon is inserted into the target vessel ōstium and inflated.

The novel features of construction and operation of the invention will be more clearly apparent during the course of the following description, reference being made to the accompanying drawings wherein a preferred form of the device has been illustrated and wherein like characters of reference are employed to denote like parts throughout the drawings.

DESCRIPTION OF THE PREFERRED EMBODIMENTS

Figure 1:
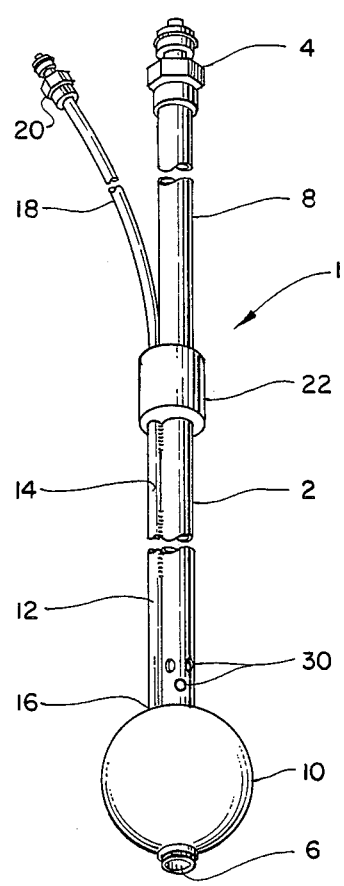
FIG. 1 is a perspective view of a guiding catheter constructed in accordance with the invention disclosed and claimed herein.

Referring to the drawings, where like numbers of reference indicate like elements throughout, there has been illustrated a preferred embodiment of a guiding catheter generally referred to as 1 constructed in accordance with the invention disclosed herein.

Generally, as illustrated in FIG. 1, guiding catheter 1 comprises a first hollow tubular body 2 of flexible non-kinking material having an entry port connector 4, an exit port 6, and a first lumen 8 therethrough.

A fixation balloon 10 of soft elastomeric material is attached coaxially to first hollow tubular body 2 proximate exit port 6. Fixation balloon 10 may have an inflated shape adapted to resist backward or rearward movement of exit port 6 and the guiding catheter generally from an opening, as a vessel ostium, once fixation balloon 10 is inserted into such opening and inflated.

A second hollow tubular body 12 of flexible, non-kinking material has a second lumen 14 therethrough. Second hollow tubular body 12 is operatively attached at one end 16 to fixation balloon 10 and at an opposite second end 18 to a port connector 20. Port connector 20 may be any of the commonly available connectors such as a Luer connector that are widely available for use. Second lumen 14 may be joined to either the outer or inner surface of first hollow tubular body 2 by heat sealing or adhesive bonding. Likewise, second lumen 14 may be integrally formed with first hollow tubular body 2 in accordance with existing fabrication methods. Second lumen 14 may also in some cases be preferably contained within or formed by the substance forming the wall of first hollow tubular body 2, and therefore be neither truly on the inner nor on the outer surface of hollow tubular body 2.

A strengthening plug molding 22 is illustrated in the drawings to prevent structural separation of the first and second hollow tubular bodies, 2 and 12 respectively. Plug molding 22 is adapted to add to the structural integrity of the catheter assembly 1.

Figure 2:
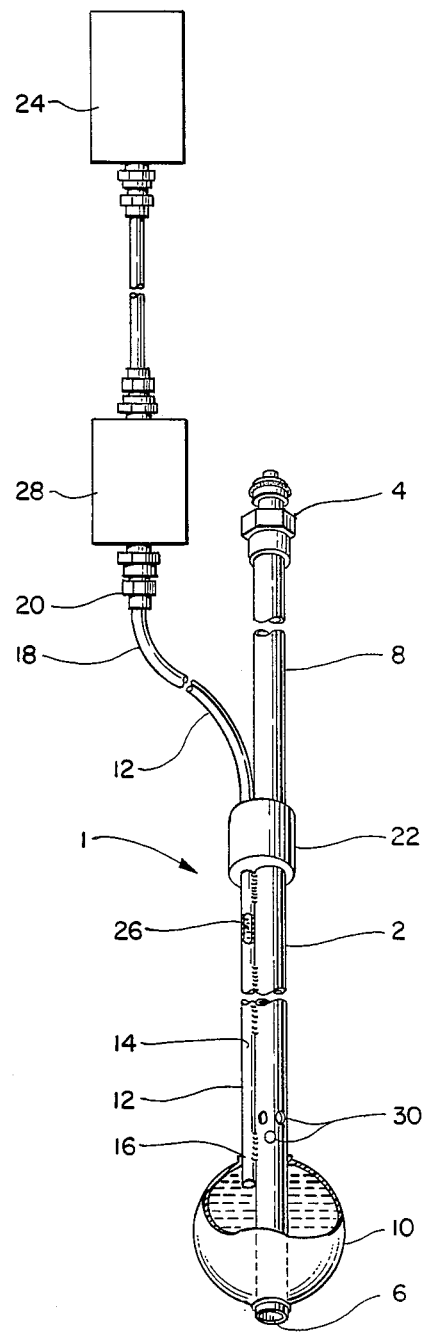
FIG. 2 is a perspective view of a guiding catheter constructed in accordance with the invention disclosed and claimed herein further showing operatively connected thereto both the pressure limiting means and the pressure means for inflation and deflation of the fixation balloon.

FIG. 2 illustrates how port connector 20 of second hollow tubular body 12 is operatively coupled to means 24 to selectively inflate and deflate fixation balloon 10 by applying pressure to a liquid 26 contained in second lumen 14.

Also operatively coupled between port connector 20 and means 24 is means 28 adapted to limit the pressure supplied to inflate fixation balloon 10 through second lumen 14 to a selected pre-set pressure limit. Means 28 may be any of the commonly available pressure limiting devices, such as a manometer or pressure release valve, currently in use in surgical and angiographic procedures. Similarly, means 24 may be a mechanical or hand operated pressure source as is currently in widespread surgical and angiographic use.

Liquid 26 is preferable to a gaseous medium in transmitting the pressure forces to fixation balloon 10, since the use of a gaseous medium poses a generally unacceptable risk of damage or death to a patient were the fixation balloon 10 or the second hollow tubular body 12 to rupture and the gaseous material to form a "bubble" embolus in the circulatory system, which might cause disruption of normal circulatory flow therethrough. Preferably liquid 26 is a dilute mixture of a radiographic contrast agent and saline, or any other safe non-toxic liquid. Thus, even were a rupture to occur in the fixation balloon/second hollow tubular body pressure system and the liquid to enter the patient's circulatory system, no harm or disruption of circulatory flow would ensue.

Similarly, when the device of the invention is to be used in many surgical and angiographic procedures, it is preferred that first hollow tubular body 2 should be provided with a means to allow continued circulatory system flow into any opening (vessel ostium) that is otherwise blocked by fixation balloon 10 and exit port 6. One preferred means to accomplish this objective is to have first hollow tubular body 2 comprised of a porous material adapted to permit fluid flow therethrough. A second preferred means, illustrated in the drawings, is to have a plurality of holes or apertures 30 in first hollow tubular body 2 proximate exit port 6 and fixation balloon 10. As shown in the drawings, such apertures 30 must, of course, appear in at least the non-blocked side of first hollow tubular body 2, as when fixation balloon 10 is inserted into an opening (vessel ostium) and inflated, it effectively forms a seal blocking any flow around it into the opening (vessel ostium).

Likewise, there are some procedures for which the device of the invention may be used not directed toward manipulation of PTCA/PTA catheters in blood vessels, such as, angioplasty in vascular structures other than blood vessels (e.g., bile ducts in the liver) or the delivery of embolic material for the therapeutic embolization (occlusion) of a blood vessel when it would be preferable (or inconsequential) to stop circulatory flow in a vessel. Guiding catheters intended for such uses would be constructed of non-porous material and would not contain side holes.

The invention described above is, of course, susceptible to many variations, modifications and changes, all of which are within the skill of the art. It should be understood that all such variations, modifications and changes are within the spirit and scope of the invention and of the appended claims. Similarly, it will be understood that it is intended to cover all changes, modifications and variations of the example of the invention disclosed herein for the purpose of illustration which do not constitute departures from the spirit and scope of the invention.

I claim:

1. A guidance catheter system of a size to fit within the human vascular or coronary system for providing a stabilizing platform proximate the ostium of a vessel that will minimize trauma and edema to the tissue of the vessel walls forming the ostium of the vessel, for inserting and guiding a surgical catheter therethrough and into the vessel to a selected position, comprising:

a first hollow tubular body of semi-rigid, non-kinking material having an entry and an exit port and a first lumen therethrough, said first lumen having a diameter sufficient to permit the free passage therethrough of the surgical catheter inserted thereinto at said entry port so that it may exit therefrom at said exit port of said first hollow tubular body into the vessel;

a fixation balloon of soft elastomeric material surrounding said first hollow tubular body proximate said exit port;

a second hollow tubular body of semi-rigid non-kinking material attached in a lengthwise fashion to said first hollow tubular body and having a second lumen therethrough, said second hollow tubular body operatively attached at one end to said fixation balloon, and at an opposite second end connected to a source of liquid for selectively inflating and deflating said fixation balloon by applying a pressure differential to liquid applied to said second lumen, said second lumen providing a passageway for communicating said liquid under pressure to selectively inflate and deflate said fixation balloon;

limiting means operatively coupled between said second hollow tubular body and said source of liquid for limiting the pressure differential applied to selectively inflate and deflate said fixation balloon to a selected pre-set limit that is sufficient to resist dislodging of said fixation balloon from the vessel ostium by the passage of the surgical catheter through said first lumen of said first hollow tubular body, and insufficient to cause dilation injury to the tissues forming the wall of the vessel ostium surrounding said fixation balloon when said fixation balloon is fully inflated; and a plurality of fluid passageway means extending from said exit port of said first hollow tubular body to the exterior surface thereof adjacent to and on the opposite side of said fixation balloon for communicating fluid contained in the vessel around said inflated fixation balloon, said fluid passageway means having a diameter less than that of said first lumen so as to be adapted to prevent the exit therethrough of the surgical catheter as it is advanced through said first lumen of said first hollow tubular body, whereby when said exit port of said first hollow tubular body is inserted into and positioned proximate the inside portion of a vein proximate a selected vascular ostium and said fixation balloon is inflated to said pre-set pressure limit to form an anatomically conforming seal against the inner walls of said vein, thereby holding said exit port of said first hollow tubular body in position, said guidance catheter system provides a stable guiding passageway through said first lumen of said first hollow tubular body for inserting and guiding an angioplasty catheter therethrough and into said vascular ostium.

2. A guidance catheter system as in claim 1 wherein said first hollow tubular body is comprised of a non-porous material.

3. A guidance catheter system as in claim 1 wherein said plurality of fluid passageway means includes a plurality of holes in said first hollow tubular body proximate said fixation balloon.

4. A guidance catheter system as in claim 3 wherein said liquid communicating the pressure differential to inflate and deflate said fixation balloon is a safe, non-toxic liquid.

5. A guidance catheter system as in claim 4 wherein said safe, non-toxic liquid is a dilute mixture of a radiographic contrast agent and saline.

6. A guidance catheter system as in claim 5 wherein said fixation balloon has an inflated shape adapted to resist backward movement of said first hollow tubular body from the vessel ostium once said fixation balloon is inserted into said vessel ostium and inflated to said pre-set inflation limit.

7. A guidance catheter system as in claim 1 wherein said second hollow tubular body is attached in a lengthwise fashion to said first hollow tubular body on the outer surface of said first hollow tubular body.

8. A guidance catheter system as in claim 1 wherein said second hollow tubular body is attached in a lengthwise fashion to said first hollow tubular body on the inner surface of said first hollow tubular body.

9. A guidance catheter system as in claim 1 wherein said second hollow tubular body is attached in a lengthwise fashion to said first hollow tubular body on the outer surface of said first hollow tubular body by being integrally formed therewith.

10. A guidance catheter system as in claim 1 wherein said second hollow tubular body is attached in a lengthwise fashion to said first hollow tubular body on the inner surface of said first hollow tubular body by being integrally formed therewith.

11. A guidance catheter system as in claim 1 wherein said second hollow tubular body is disposed within the material forming the wall of said first hollow tubular body.

12. A guidance catheter system of a size to fit within the human vascular or coronary system for providing a stabilizing platform proximate the ostium of a vessel that will minimize trauma and edema to the tissue of the vessel walls forming the ostium of the vessel, for inserting and guiding a surgical catheter therethrough and into the vessel to a selected position, comprising:

a first hollow tubular body of semi-rigid, non-kinking porous material having an entry and an exit port and a single first lumen therethrough, said first lumen having a diameter sufficient to permit the free passage therethrough of the surgical catheter inserted thereinto at said entry port so that it may exit therefrom at said exit port of said first hollow tubular body into the vessel;

a single fixation balloon of soft elastomeric material surrounding said first hollow tubular body proximate said exit port;

a second hollow tubular body of semi-rigid non-kinking material attached in a lengthwise fashion to said first hollow tubular body and having a second lumen therethrough, said second hollow tubular body operatively attached at one end to said fixation balloon, and at an opposite second end connected to a source of liquid for selectively inflating and deflating said fixation balloon by applying a pressure differential to liquid applied to said second lumen, said second lumen providing a passageway for communicating said liquid under pressure to selectively inflate and deflate said fixation balloon;

limiting means operatively coupled between said second hollow tubular body and said source of liquid for limiting the pressure differential applied to selectively inflate and deflate said fixation balloon to a selected pre-set limit that is sufficient to resist dislodging of said fixation balloon from the vessel ostium by the passage of the surgical catheter through said first lumen of said first hollow tubular body, and insufficient to cause dilation injury to the tissues forming the wall of the vessel ostium surrounding said fixation balloon when said fixation balloon is fully inflated; and a plurality of fluid passageway means extending from said exit port of said first hollow tubular body to the exterior surface thereof adjacent to and on the opposite side of said fixation balloon for communicating fluid contained in the vessel around said inflated fixation balloon, said fluid passageway means having a diameter less than that of said first lumen so as to be adapted to prevent the exit therethrough of the surgical catheter as it is advanced through said first lumen of said first hollow tubular body, whereby when said exit port of said first hollow tubular body is inserted into and positioned proximate the inside portion of a vein proximate a selected vascular ostium and said fixation balloon is inflated to said pre-set pressure limit to form an anatomically conforming seal against the inner walls of said vein, thereby holding said exit port of said first hollow tubular body in position, said guidance catheter system provides a stable guiding passageway through said first lumen of said first hollow tubular body for inserting and guiding an angioplasty catheter therethrough and into said vascular ostium.

* * * * *